United States Patent
Mou et al.

(10) Patent No.: US 10,382,841 B2
(45) Date of Patent: Aug. 13, 2019

(54) DRIVING AND INFORMATION TRANSMITTING SYSTEM FOR SENSING MODULE

(71) Applicant: Microjet Technology Co., Ltd., Hsinchu (TW)

(72) Inventors: Hao-Jan Mou, Hsinchu (TW); Ta-Wei Hsueh, Hsinchu (TW); Li-Pang Mo, Hsinchu (TW); Shih-Chang Chen, Hsinchu (TW); Ching-Sung Lin, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 0 days.

(21) Appl. No.: 16/015,584

(22) Filed: Jun. 22, 2018

(65) Prior Publication Data
US 2019/0037284 A1    Jan. 31, 2019

(30) Foreign Application Priority Data
Jul. 27, 2017  (TW) .............................. 106125334 A

(51) Int. Cl.
*H04Q 9/00*     (2006.01)
*G01N 33/00*    (2006.01)
(Continued)

(52) U.S. Cl.
CPC ........... *H04Q 9/00* (2013.01); *G01N 33/0062* (2013.01); *G01N 33/0073* (2013.01);
(Continued)

(58) Field of Classification Search
CPC .. H04Q 9/00; H04Q 2209/88; H04Q 2209/40; G01N 33/0062; G01N 33/0073; G08B 21/12
(Continued)

(56) References Cited

U.S. PATENT DOCUMENTS 9,332,322 B2 * 5/2016 Niemeyer ................ H04Q 9/00
2007/0069905 A1   3/2007 Wang
(Continued)

FOREIGN PATENT DOCUMENTS

TW            I547810 B       9/2016
TW          201700973 A       1/2017
WO    WO 2014/093882 A1       6/2014

OTHER PUBLICATIONS

Extended European Search Report, dated Jan. 14, 2019, for European Application No. 18179242.5.

*Primary Examiner* — Hirdepal Singh
(74) *Attorney, Agent, or Firm* — Birch, Stewart, Kolasch & Birch, LLP

(57) ABSTRACT

A driving and information transmitting system for a sensing module includes a sensing device, a power supply device and a connection device. The sensing device includes a sensor, a microprocessor, a power controller and a data transceiver. The power supply device transfers an energy to the power controller, thereby enabling the sensor. After a monitored data sensed by the at least one sensor is transmitted to the microprocessor, the monitored data is processed into an output data by the microprocessor. After the output data is received by the data transceiver, the output data is transmitted from the data transceiver to the connection device. After a control command from the connection device is received by the data transceiver, the control command is transmitted to the microprocessor to control the sensor.

18 Claims, 1 Drawing Sheet

(51) Int. Cl.
  *G08B 21/12*   (2006.01)
  *F04B 35/04*   (2006.01)
(52) U.S. Cl.
  CPC .............. *G08B 21/12* (2013.01); *F04B 35/04* (2013.01); *H04Q 2209/40* (2013.01); *H04Q 2209/88* (2013.01)
(58) Field of Classification Search
  USPC .................................................. 340/870.07
  See application file for complete search history.

(56) References Cited

U.S. PATENT DOCUMENTS

| | | |
|---|---|---|
| 2009/0128326 A1 | 5/2009 | Hong |
| 2014/0349707 A1 | 11/2014 | Bang |
| 2015/0380971 A1 | 12/2015 | Priev et al. |
| 2016/0171869 A1 | 6/2016 | Gullbrand et al. |
| 2017/0031337 A1* | 2/2017 | Jablokov ................ G08C 17/02 |
| 2017/0171692 A1* | 6/2017 | Shinohara ............... H04W 4/70 |
| 2017/0287308 A1* | 10/2017 | Takeda .................... H04W 4/70 |
| 2018/0120279 A1* | 5/2018 | Yi ...................... G01N 33/0073 |
| 2018/0139517 A1* | 5/2018 | Schwartz ................. H04Q 9/00 |
| 2018/0270632 A1* | 9/2018 | Kaneeda ................ G08C 17/02 |
| 2018/0271499 A1* | 9/2018 | Toriumi ................... A61B 8/00 |
| 2019/0056368 A1* | 2/2019 | Mou .................... G01D 11/245 |

* cited by examiner

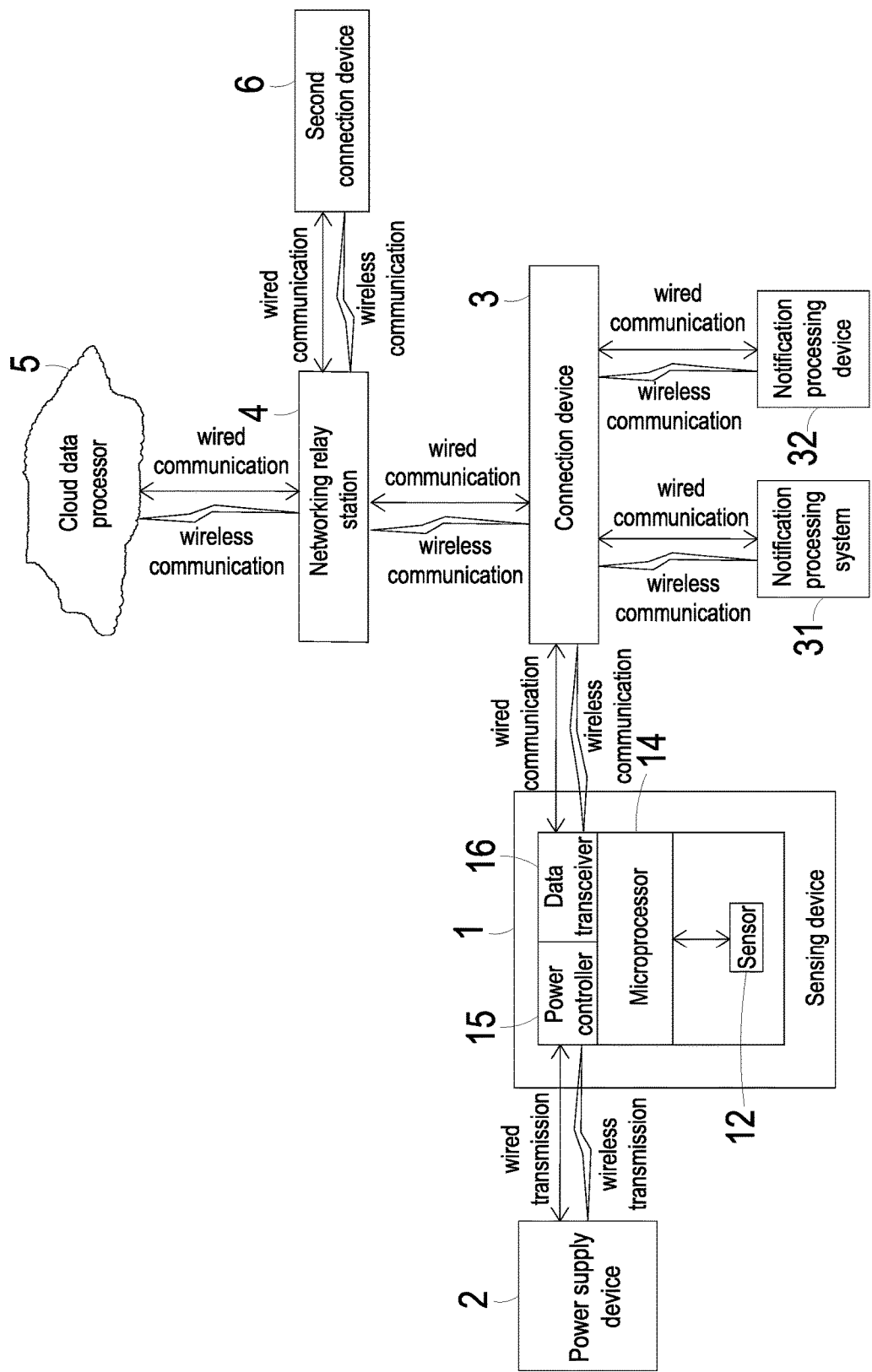

DRIVING AND INFORMATION TRANSMITTING SYSTEM FOR SENSING MODULE

FIELD OF THE INVENTION

The present disclosure relates to a sensing module utilizing in environmental monitoring, and more particularly to a driving and information transmitting system for a sensing module.

BACKGROUND OF THE INVENTION

Nowadays, people pay much attention to monitoring environmental air quality in daily living, e.g., monitoring carbon monoxide, carbon dioxide, volatile organic compounds (VOC), PM2.5, and so on. The exposure of these gases or substances in the environment can cause human health problems or can even harm the life. Therefore, it has become an important issue for every country to develop and implement environmental air quality monitoring technology.

Generally, it is feasible to use a sensor to monitor the air quality in the environment. If the sensor can further provide immediate monitored information for the people in the environment, the people can be alerted to take precautions or escape promptly, thus the negative influence on human body and injury to the health caused by the exposure to the harmful gas are prevented. In this regard, the sensor is suitably used for monitoring the environment.

Nowadays, there are large-scale environmental monitoring base stations provided to monitor environmental air quality. However, those base stations are only suitable for monitoring air quality in a large area, which are unable to promptly monitor the quality of the air surrounding a human being with precision and efficiency, e.g., the indoor air quality or the ambient air close to the human being. If the sensor is integrated into a portable electronic device, the air quality can be real-time monitored in everywhere and at any time. Moreover, the monitored data can be transmitted to a cloud database in real time for database construction and data integration. Consequently, the monitored data of the air quality can be more accurately and immediately provided for enabling an air quality notification mechanism and an air quality processing mechanism.

Therefore, there is a need of providing a solution for immediately monitoring the air quality in everywhere and at any time, transmitting the monitored data to the cloud database for database construction and data integration, providing more accurately and immediately monitored data, and enabling the air quality notification mechanism and the air quality processing mechanism.

SUMMARY OF THE INVENTION

An object of the present disclosure is to provide a driving and information transmitting system for a sensing module. The system includes a sensing device, a power supply device and a connection device. The sensing device includes at least one sensor, a microprocessor, a power controller and a data transceiver integrated as a modular structure. The sensing device is not necessarily equipped with a power source since the sensing device is in connection with the power supply device, in which the power supply device transfers energy to power the sensor, the power controller, the data transceiver and the microprocessor. Therefore, the installation space of the overall modular structure is saved, and the purpose of minimizing the modular structure is achieved, so that the modular structure can be applied to an electronic device for monitoring the air quality. The sensing module uses the data transceiver to receive a control command for enabling the sensor to perform the sensing operation. After a monitored data sensed by the sensor is transmitted to the microprocessor, the monitored data is processed into an output data. The output data is transmitted to the connection device by the data receiver, so that the information carried by the output data can be displayed, stored and transmitted by the connection device. Consequently, the purpose of immediately displaying the monitoring information and immediately issuing the notification signal are achieved. Moreover, the output data can be transmitted to a cloud database for database construction and data integration. Consequently, the monitored data of the air quality can be more accurately and immediately provided for enabling an air quality notification mechanism and an air quality processing mechanism.

In accordance with an aspect of the present disclosure, a driving and information transmitting system for a sensing module is provided. The system includes a sensing device, a power supply device and a connection device. The sensing device includes at least one sensor, a microprocessor, a power controller and a data transceiver. The power supply device transfers an energy to the power controller, so that the power controller receives the energy and enables the at least one sensor. After a monitored data sensed by the at least one sensor is transmitted to the microprocessor, the monitored data is processed into an output data by the microprocessor. After the output data is received by the data transceiver, the output data is transmitted from the data transceiver to the connection device. After a control command from the connection device is received by the data transceiver, the control command is transmitted to the microprocessor to control the at least one sensor to perform a sensing operation.

The above contents of the present disclosure will become more readily apparent to those ordinarily skilled in the art after reviewing the following detailed description and accompanying drawings, in which:

BRIEF DESCRIPTION OF THE DRAWINGS

FIG. 1 schematically illustrates the architecture of a driving and information transmitting system for a sensing module according to an embodiment of the present disclosure.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Please refer to FIG. 1. The present discourse provides a driving and information transmitting system for a sensing module, in which the driving and information transmitting system includes at least one sensing device 1, at least one sensor 12, at least one microprocessor 14, at least one power controller 15, at least one data transceiver 16, at least one power supply device 2, at least one energy, at least one connection device 3, at least one output data, and at least one control command. The number of the sensing device 1, the microprocessor 14, the power controller 15, the data transceiver 16, the power supply device 2, the energy, the connection device 3, the output data and the control command is exemplified by one for each in the following embodiments but not limited thereto. It is noted that each of the sensing device 1, the microprocessor 14, the power controller 15, the data transceiver 16, the power supply device 2, the energy, the connection device 3, the output data and the control command can also be provided in plural numbers.

FIG. 1 schematically illustrates the architecture of a driving and information transmitting system for a sensing module according to an embodiment of the present disclosure. As shown in FIG. 1, the driving and information transmitting system for the sensing module includes a sensing device 1, a power supply device 2 and a connection device 3. The sensing device 1 includes at least one sensor 12, a microprocessor 14, a power controller 15 and a data transceiver 16. The power controller 15 receives an energy and transfers the energy to enable the sensor 12. The data transceiver 16 can receive or transmit data.

An example of the sensor 12 includes but is not limited to a temperature sensor, a volatile organic compound sensor (e.g., a sensor for measuring formaldehyde or ammonia gas), a particulate sensor (e.g., a PM2.5 particle sensor), a carbon monoxide sensor, a carbon dioxide sensor, an oxygen sensor, an ozone sensor, any other appropriate gas sensor, a humidity sensor, a water content sensor, a substance sensor (e.g., a sensor for measuring compounds or biological substances in liquid or air), a water quality sensor, any other appropriate liquid sensor, a light sensor, or the combination thereof.

The power supply device 2 transfers energy to the power controller 15. After the power controller 15 receives the energy, the power controller 15 enables the sensor 12. In some embodiments, the energy is a light energy, an electric energy, a magnetic energy, a sound energy or a chemical energy, but not limited thereto.

In an embodiment, the power supply device 2 transfers power to the power controller 15 in a wired transmission manner. For example, the power supply device 2 is a charger or a rechargeable battery capable of transferring energy to the power controller 15 in the wired transmission manner. In another embodiment, the power supply device 2 transfers power to the power controller 15 in a wireless transmission manner. For example, the power supply device 2 is a charger or a rechargeable battery with a wireless charging component (or an induction charging component), and is capable of transferring energy to the power controller 15 in the wireless transmission manner. In further another embodiment, the power supply device 2 is a portable mobile device with wireless charging/discharging function, e.g., a smart phone having a wireless charging component (or an induction charging component), and is capable of transferring energy to the power controller 15 in the wireless transmission manner.

In an embodiment, the power controller 15 further includes a chargeable element (not shown) for receiving and storing the energy. The chargeable element of the power controller 15 receives the energy from the power supply device 2 transferred through a wired transmission path or a wireless transmission path. Then, the chargeable element stores the energy, and outputs the energy to the sensor 12 for powering the sensor 12 to perform a sensing operation.

The sensor 12 is used for monitoring the environment to acquire a monitored data. The microprocessor 14 processes and calculates the monitored data to convert the monitored data to an output data. The data transceiver 16 receives the output data, and sends it to the connection device 3 through transmission, so that the connection device 3 can display and store the information carried by the output data, or can transmit the information carried by the output data to a storage device (not shown) of the connection device 3 for storing or processing. In an embodiment, the connection device 3 is in communication with a notification processing system 31 to actively (i.e. directly notify) or passively (i.e. operated by a user to whom the information carried by the output data is provided) enable an air quality notification mechanism, e.g., an instant air quality map informs people to avoid away or to wear masks. In another embodiment, the connection device 3 is in communication with a notification processing device 32 to actively (i.e. directly operate) or passively (i.e. operated by a user to whom the information carried by the output data is provided) enable an air quality processing mechanism, e.g., an air cleaner or an air-conditioner is enabled to clean the air.

In an embodiment, the connection device 3 is a display device with a wired communication module (e.g., a desktop computer). In another embodiment, the connection device 3 is a display device with a wireless communication module (e.g., a notebook computer). In another embodiment, the connection device 3 is a portable electronic device with a wireless communication module (e.g., a mobile phone). For example, the wired communication module has an RS485 communication port, an RS232 communication port, a Modbus communication port or a KNX communication port, and the wireless communication module performs a wireless communication process according to a Zigbee communication technology, a Z-wave communication technology, an RF communication technology, a Bluetooth communication technology, a Wifi communication technology or an EnOcean communication technology.

The driving and information transmitting system for the sensing module further includes a networking relay station 4 and a cloud data processor 5. The connection device 3 sends the information carried by the output data to the networking relay station 4, after which the networking relay station 4 sends the information carried by the output data to the cloud data processor 5 to make it stored and processed in the cloud data processor 5. The cloud data processor 5 processes the information carried by the output data and issues a notification signal to the connection device 3 through the networking relay station 4. After the connection device 3 receives the notification signal, the notification processing system 31 connected with the connection device 3 enables an air quality notification mechanism in response to the notification signal. Alternatively, the notification processing device 32 connected with the connection device 3 receives the notification signal from the connection device 3, and accordingly enables an air quality processing mechanism.

In an embodiment, the connection device 3 issues a control command to the sensing device 1 so as to control the operation of the sensing device 1. Similarly, the control command is transmitted to the data transceiver 16 in the wired or wireless communication transmission manner as discussed above. Then, the control command is transmitted to the microprocessor 14 to control the sensor 12 to perform the sensing operation.

In an embodiment, the driving and information transmitting system for the sensing module further includes a second connection device 6. The second connection device 6 can issue a control command to the cloud data processor 5 through the networking relay station 4, after which the control command is transmitted from the cloud data processor 5 to the connection device 3 through the networking relay station 4. Then, the connection device 3 issues the control command to the data transceiver 16 of the sensing module 1. After the data transceiver 16 receives the control command, the data transceiver 16 transmits the control command to the microprocessor 14. According to the control command, the microprocessor 14 controls the sensor 12 to perform the sensing operation. In this embodiment, the second connection device 6 may be a device with a wired communication transmission module, a device with a wireless communication transmission module, or a portable mobile device with a wireless communication transmission module, but not limited thereto.

From the above description, since the driving and information transmitting system for the sensing module includes the power supply device 2 for providing power, the sensing device 1 is not necessarily equipped with the power source. The power supply device 2 transfers energy to power the sensor 12, the power controller 15, the data transceiver 16 and the microprocessor 14. Since the installation space of the overall modular structure is saved, the purpose of minimizing the modular structure is achieved so that the modular structure is suitably applied to an electronic device for monitoring the air quality. Moreover, the data transceiver 16 can receive a control command for controlling the sensor 12 to perform the sensing operation. After the monitored data sensed by the at least one sensor 12 is transmitted to the microprocessor 14, the monitored data is processed into an output data. The output data is transmitted to the connection device 3, so that the information carried by the output data can be displayed, stored and transmitted by the connection device 3. Consequently, the function of immediately displaying the monitoring information and immediately issuing the notification signal are achieved. Furthermore, the output data can be transmitted to a cloud database for database construction and data integration. Consequently, the monitored data of the air quality can be more accurately and immediately provided for enabling an air quality notification mechanism and an air quality processing mechanism.

In sum, the present disclosure provides a driving and information transmitting system for the sensing module, the system includes a sensing device, a power supply device and a connection device. The sensing device includes at least one sensor, a microprocessor, a power controller and a data transceiver, which are integrated as a modular structure. The sensing device is not necessarily equipped with the power source since the sensing device is in connection with the power supply device, in which the power supply device transfers energy to power the sensor, the power controller, the data transceiver and the microprocessor. Therefore, the installation space of the overall modular structure is saved, and the purpose of minimizing the modular structure is achieved, so that the modular structure is suitably applied to an electronic device for monitoring the air quality.

In addition, the sensing device uses the data transceiver to receive a control command for enabling the sensor to perform the sensing operation. After a monitored data sensed by the at least one sensor is transmitted to the microprocessor, the monitored data is processed into an output data. The output data is transmitted to the connection device by the data transceiver, so that the information carried by the output data can be displayed, stored and transferred by the connection device. Consequently, the function of immediately displaying the monitoring information and immediately issuing the notification signal are achieved. Moreover, the output data can be transmitted to a cloud database for database construction and data integration. Consequently, the monitored data of the air quality can be more accurately and immediately provided for enabling an air quality notification mechanism and an air quality processing mechanism.

While the disclosure has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A driving and information transmitting system for a sensing module, the driving and information transmitting system comprising:
   a sensing device comprising at least one sensor, a microprocessor, a power controller and a data transceiver;
   a power supply device configured to transfer an energy to the power controller, so that the power controller receives the energy and enables the sensor; and
   a connection device configured to display, store and transmit an output data,
   wherein after a monitored data sensed by the at least one sensor is transmitted to the microprocessor, the monitored data is processed into the output data by the microprocessor, wherein the output data is received by the data transceiver, and the output data is transmitted from the data transceiver to the connection device, wherein a control command from the connection device is received by the data transceiver, and the control command is transmitted to the microprocessor to control the sensor to perform a sensing operation, and the connection device is connected with a notification processing system and/or a notification processing device, so as to enable an air quality notification mechanism by the notification processing system and/or enable an air quality processing mechanism by the notification processing device.

2. The driving and information transmitting system for the sensing module according to claim 1, wherein the power supply device is a charger.

3. The driving and information transmitting system for the sensing module according to claim 1, wherein the power supply device is a rechargeable battery.

4. The driving and information transmitting system for the sensing module according to claim 1, wherein the sensing device further comprises a chargeable element.

5. The driving and information transmitting system for the sensing module according to claim 1, wherein the connection device is a display device with a wired communication module or a display device with a wireless communication module.

6. The driving and information transmitting system for the sensing module according to claim 1, wherein the connection device is a portable mobile device with a wireless communication module.

7. The driving and information transmitting system for the sensing module according to claim 1, further comprising a networking relay station, wherein the output data is transmitted from the connection device to the networking relay station.

8. The driving and information transmitting system for the sensing module according to claim 7, further comprising a cloud data processor, wherein the networking relay station transmits the output data to the cloud data processor, and the output data is processed by and stored in the cloud data processor.

9. The driving and information transmitting system for the sensing module according to claim 8, wherein after the output data is processed by the cloud data processor, the cloud data processor issues a notification signal to the networking relay station and then the notification signal is transmitted to the connection device connected with a notification processing system to enable an air quality notification mechanism.

10. The driving and information transmitting system for the sensing module according to claim 8, wherein after the output data is processed by the cloud data processor, the cloud data processor issues a notification signal to the networking relay station and then the notification signal is transmitted to the connection device connected with a notification processing device to enable an air quality processing mechanism.

11. The driving and information transmitting system for the sensing module according to claim 9, wherein the connection device is a display device with a wired communication module.

12. The driving and information transmitting system for the sensing module according to claim 9, wherein the connection device is a display device with a wireless communication module.

13. The driving and information transmitting system for the sensing module according to claim 9, wherein the connection device is a portable mobile device with a wireless communication module.

14. The driving and information transmitting system for the sensing module according to claim 8, further comprising a second connection device, wherein after the second connection device issues the control command to the cloud data processor through the networking relay station, the control command is transmitted from the cloud data processor to the connection device through the networking relay station, so that the connection device issues the control command to the data transceiver.

15. The driving and information transmitting system for the sensing module according to claim 14, wherein the second connection device is a device with a wired communication module.

16. The driving and information transmitting system for the sensing module according to claim 14, wherein the second connection device is a device with a wireless communication module.

17. The driving and information transmitting system for the sensing module according to claim 14, wherein the second connection device is a portable mobile device with a wireless communication module.

18. A driving and information transmitting system for a sensing module, the driving and information transmitting system comprising:
at least one sensing device comprising at least one sensor, at least one microprocessor, at least one power controller and at least one data transceiver;
at least one power supply device configured to transfer at least one energy to the power controller, so that the power controller receives the energy and enables the sensor; and
at least one connection device configured to display, store and transmit at least one output data,
wherein after at least one monitored data sensed by the sensor is transmitted to the microprocessor, the monitored data is processed into the output data by the microprocessor, wherein the output data is received by the data transceiver, and the output data is transmitted from the data transceiver to the connection device, wherein at least one control command from the connection device is received by the data transceiver, and the control command is transmitted to the microprocessor to control the sensor to perform a sensing operation, and the connection device is connected with at least one notification processing system and/or at least one notification processing device, so as to enable at least one air quality notification mechanism by the notification processing system and/or enable at least one air quality processing mechanism by the notification processing device.

* * * * *